United States Patent
Le Reverend et al.

(10) Patent No.: US 8,108,044 B2
(45) Date of Patent: Jan. 31, 2012

(54) METHOD AND APPARATUS FOR THE STAGED DETECTION OF RF ENERGY

(75) Inventors: Remi Le Reverend, San Diego, CA (US); Guy A. Delight, Escondido, CA (US)

(73) Assignee: Medtronic, Inc., Minneapolis, MN (US)

( * ) Notice: Subject to any disclaimer, the term of this patent is extended or adjusted under 35 U.S.C. 154(b) by 699 days.

(21) Appl. No.: 12/242,782

(22) Filed: Sep. 30, 2008

(65) Prior Publication Data

US 2009/0248116 A1    Oct. 1, 2009

Related U.S. Application Data

(60) Provisional application No. 61/040,001, filed on Mar. 27, 2008.

(51) Int. Cl.
*A61N 1/368* (2006.01)

(52) U.S. Cl. .......................................... 607/32

(58) Field of Classification Search .............. 607/30–32, 607/59–60
See application file for complete search history.

(56) References Cited

U.S. PATENT DOCUMENTS

| | | |
|---|---|---|
| 4,160,955 A | 7/1979 | Sato |
| 4,194,156 A | 3/1980 | Sakabe |
| 4,562,404 A | 12/1985 | Futakuchi |
| 4,676,248 A | 6/1987 | Berntson |
| 4,777,659 A | 10/1988 | Lindemeier et al. |
| 4,914,715 A | 4/1990 | Miyata |
| 5,132,799 A | 7/1992 | Gakumura |
| 5,350,407 A | 9/1994 | McClure et al. |
| 5,423,085 A | 6/1995 | Lim |
| 6,072,997 A | 6/2000 | Kawai |
| 7,127,218 B2 | 10/2006 | Lindenmeier |
| 7,957,813 B1 * | 6/2011 | Persson et al. ............ 607/60 |
| 2001/0041551 A1 | 11/2001 | Rotzoll |
| 2003/0114897 A1 | 6/2003 | Von Arx et al. |
| 2003/0114898 A1 | 6/2003 | Von Arx et al. |

(Continued)

FOREIGN PATENT DOCUMENTS

EP    0656701    6/1995

(Continued)

OTHER PUBLICATIONS

International Search Report, PCT/US2009/037096, 4 pages.

(Continued)

*Primary Examiner* — Scott Getzow
*Assistant Examiner* — Amanda Patton
(74) *Attorney, Agent, or Firm* — Stephen W. Bauer; Michael J. Ostrom (57) ABSTRACT

A low power method and apparatus for detecting wake-up signals in sniff processing performed in an implantable medical device (IMD) using a staged detection of RF energy in signals received in order to conserve current consumption. Incoming signals are monitored in a plurality of detection stages which each incrementally increase the accuracy of detecting whether the received signal is a wake-up communication signal. A desired number of stages of signal quantity measurements are performed such that a combined signal quantity is calculated by updating the signal quantity measurements performed in prior stages with signal quantity measurements performed at each stage. The combined signal quantity of the received communication signal is compared at each detection stage against a corresponding threshold value for that stage. The staged detection process aborts sniff processing if the combined signal quantity fails to meet the corresponding threshold value for that stage.

19 Claims, 6 Drawing Sheets

U.S. PATENT DOCUMENTS

| | | |
|---|---|---|
| 2003/0119568 A1 | 6/2003 | Menard |
| 2004/0014480 A1 | 1/2004 | Liu et al. |
| 2004/0077383 A1 | 4/2004 | Lappetelainen et al. |
| 2004/0133092 A1 | 7/2004 | Kain |
| 2004/0207464 A1 | 10/2004 | Petrovic et al. |
| 2005/0150949 A1 | 7/2005 | Goel et al. |
| 2006/0229053 A1 | 10/2006 | Sivard |
| 2007/0049991 A1 | 3/2007 | Klostermann et al. |
| 2007/0060053 A1* | 3/2007 | Haubrich et al. ............... 455/39 |
| 2007/0060976 A1 | 3/2007 | Denzene et al. |
| 2007/0153705 A1 | 7/2007 | Rosar et al. |
| 2008/0046038 A1 | 2/2008 | Hill et al. |
| 2008/0048836 A1* | 2/2008 | Bungartz et al. ........... 340/10.33 |

FOREIGN PATENT DOCUMENTS

| | | |
|---|---|---|
| EP | 1264614 | 12/2002 |

OTHER PUBLICATIONS

Zarlink ZL 70100, "Medical Transceiver Data Sheet".

* cited by examiner

METHOD AND APPARATUS FOR THE STAGED DETECTION OF RF ENERGY

RELATED APPLICATION

This application claims the benefit of and priority to U.S. Provisional Application Ser. No. 61/040,001, filed Mar. 27, 2008, entitled, "Method and Apparatus for the Staged Detection of RF Energy," the contents of which are incorporated by reference herein in its entirety.

TECHNICAL FIELD

This disclosure relates generally to the staged detection of radio frequency (RF) energy, and, more particularly, it relates to the staged detection of RF energy for ultra-low power (ULP) applications, such as implantable medical devices (IMDs).

BACKGROUND

A wide variety of IMDs have been developed in order to monitor patient conditions and deliver therapy to the patient. An IMD typically includes a hermetically sealed housing coupled to one or more leads that are surgically implanted inside a patient for sensing conditions or for administering therapy. The IMD may provide therapeutic stimulation to the patient or may deliver drugs or agents to the patient. Alternatively or additionally, the IMD may have sensing or monitoring capabilities. For example, the IMD may sense information within a patient and store the sensed information for subsequent analysis. In some cases, the sensed information may be used directly by the IMD to adjust or control the therapy that is delivered to the patent. Telemetry is used to communicate sensed information from the IMD to an external medical device so that analysis of the sensed information can be performed. Telemetry is further used to communicate information or instructions from external medical devices to the IMD. The IMD includes a telemetry module for performing such telemetry.

Special frequency bands have been allocated for implantable medical devices using RF telemetry, such as the MICS (Medical Implantable Communication Service) band ranging from 402-405 MHz and the MEDS (Medical Electronic Data Service) band that extends the range to 401-406 MHz. The limited battery capacity in IMDs presents a challenge in operating a RF transceiver at such frequencies. One manner employed to conserve power in an IMD is to maintain the IMD in an off state and operate in the so-called "sniff" mode. This means that the complete receiver RF portion of the device is turned on for a limited period of time (e.g. 10 milliseconds) during which time the device listens to see if there are any transmitters active in the vicinity wanting to make contact with the IMD. By duty cycling the on (sniff) time heavily with the off time a considerable power saving can be achieved. The signals received during these sniff operations are referred to as wake-up signals that direct the IMD to power on various components to communicate with the external medical device.

SUMMARY

In one or more embodiments, an implantable medical device (IMD) and method are provided in which a telemetry module in the IMD is normally maintained in a low power inactive "sleep" state and powered up to perform sniff operations on communication channels for detecting the presence of wake-up signals. In one or more embodiments, the IMD includes a wake-up receiver for detecting the presence of wake-up signals using a staged detection of RF energy in signals received by the wake-up receiver in order to conserve current consumption. The wake-up receiver includes a signal detector for monitoring a communication signal received by the IMD using a staged detection process to detect whether the communication signal is a wake-up signal or otherwise intended for the IMD. In one or more embodiments, the staged detection process includes a plurality of detection stages in which each detection stage incrementally increases the accuracy of detecting whether the received communication signal is a wake-up communication signal.

In one or more embodiments, the staged detection process includes performing a desired number of stages of measurements of a signal quantity of the received communication signal, wherein a combined signal quantity of the received communication signal is calculated by updating the signal quantity measurements performed in prior stages with signal quantity measurements performed at each stage. The combined signal quantity of the received communication signal is compared at each detection stage against a corresponding threshold value for that stage. The staged detection process is aborted if the combined signal quantity fails to meet the corresponding threshold value for that stage.

In one or more embodiments, the signal quantity monitored during the staged detection process is the strength of the received communication signal. The combined signal quantity is then calculated by adding the signal quantity measurement for a current stage of the staged detection process to the signal quantity measurements from prior stages, while the corresponding threshold value is scaled for the current stage of the staged detection process. The combined signal quantity of the received communication signal at the current stage of the staged detection process is compared against the scaled threshold value for that stage, and the staged detection process is aborted if the combined signal quantity fails to meet the scaled threshold value for that stage. In one or more embodiments, the signal quantity monitored during the staged detection process is a frequency deviation.

In one or more embodiments, a device and method are provided for monitoring a communication signal received in a receiver using a staged detection process to detect properties of the received communication signal. The staged detection process includes performing a desired number of stages of measurements of a signal quantity of the received communication signal, wherein a combined signal quantity of the received communication signal is calculated by updating the signal quantity measurements performed in prior stages with signal quantity measurements performed at each stage. The combined signal quantity of the received communication signal at each detection stage is compared against a corresponding threshold value for that stage, and the staged detection process is aborted if the combined signal quantity fails to meeting the corresponding threshold value for that stage.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Since the battery capacity in an IMD is very limited, the power consumed by the components of the IMD can be conserved by keeping the components in a power off or low power "sleep" state when they are not being utilized. The present disclosure describes an implantable medical device (IMD) and a method for operating the same in which communication signals received by the IMD can be sniffed using a staged detection of the RF energy of the received communications signals for detecting whether the received communication signals are wake-up signals intended for the IMD, where the staged detection process minimizes the total power consumption required to perform such detection operations. In the following description, numerous embodiments are set forth in order to provide a thorough understanding of the invention. It will be apparent, however, to one skilled in the art, that these and other embodiments may be practiced without these specific details. In some instances, features well-known to those skilled in the art have not been described in detail in order not to obscure the present disclosure.

Figure 1:
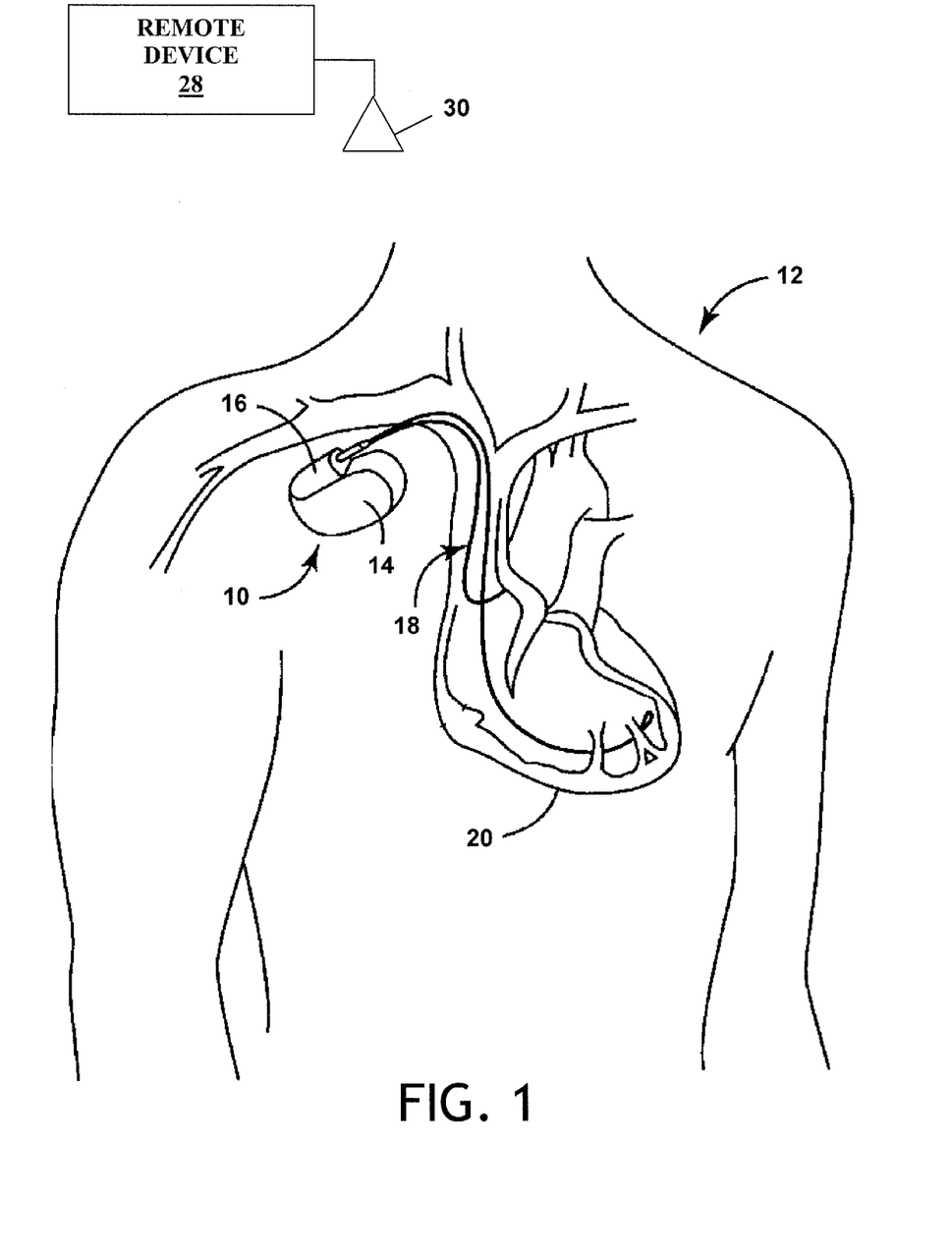
FIG. 1 illustrates an implantable medical device system in accordance with an embodiment of the present disclosure implanted in a human body.

FIG. 1 is a simplified schematic view of one embodiment of implantable medical device ("IMD") 10 of the present disclosure implanted within a human body 12. IMD 10 comprises a hermetically sealed enclosure 14 and connector module 16 for coupling IMD 10 to electrical leads 18 arranged within body 12, such as pacing and sensing leads 18 connected to portions of a heart 20 for delivery of pacing pulses to a patient's heart 20 and sensing of heart 20 conditions. While IMD 10 is depicted in a pacemaker device configuration in FIG. 1, it is understood that IMD 10 may comprise any type of implanted device including, but not limited to implantable cardioverter-defibrillators (ICDs), an implantable combination pacemaker-cardioverter-defibrillator (PCDs), implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

Figure 2:
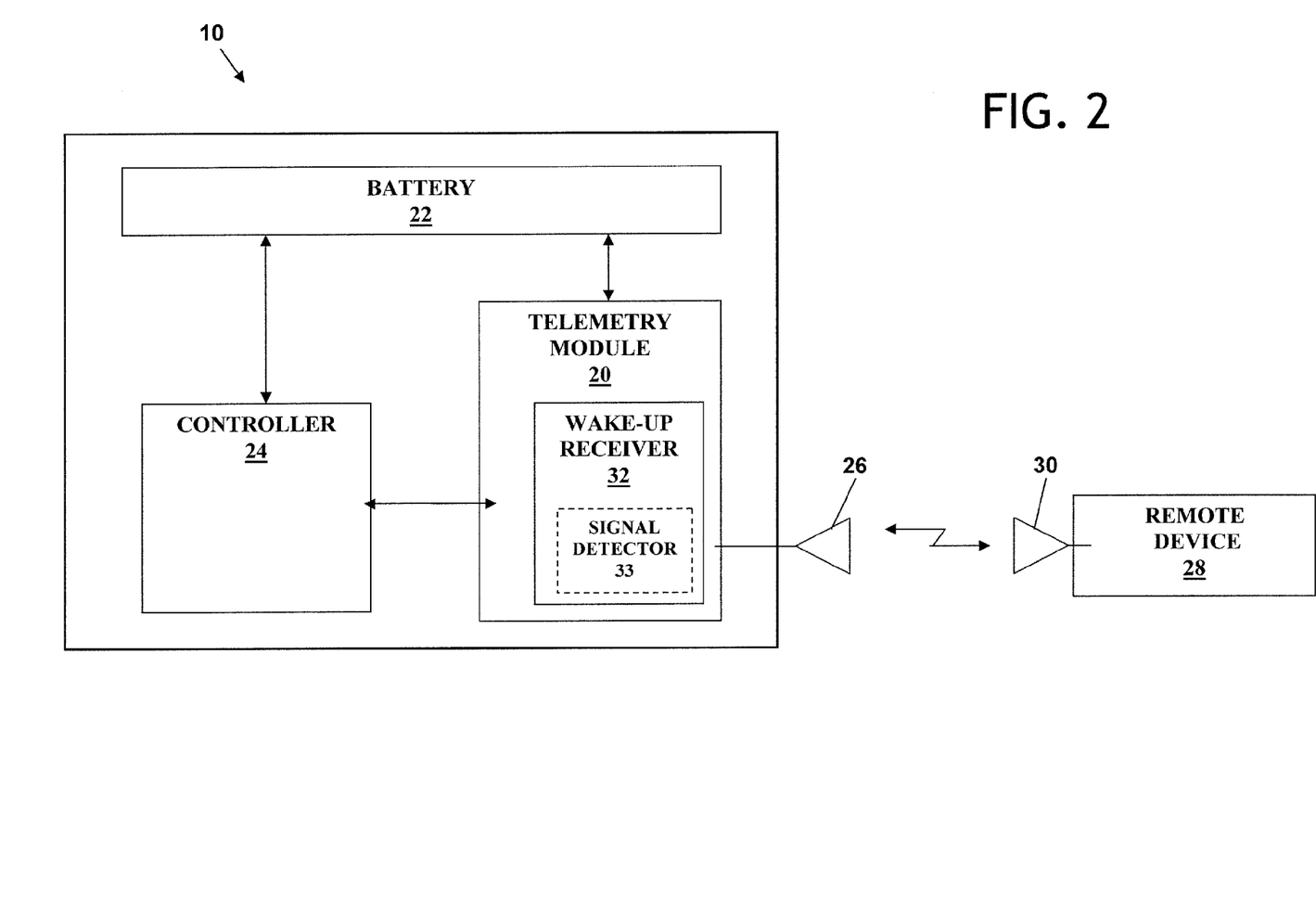
FIG. 2 is a block diagram illustrating the various components of one embodiment of an implantable medical device configured to operate in accordance with the present disclosure.

FIG. 2 is a block diagram illustrating the constituent components of IMD 10 in accordance with one embodiment having a microprocessor-based architecture. IMD 10 is shown as including a telemetry module 20, a battery 22, and a controller 24.

Telemetry module 20 may comprise any unit capable of facilitating wireless data transfer between IMD 10 and an remote device 28, where remote device 28 may comprise an external medical device, a programming device, a remote telemetry station, a base station for IMD 10, a physician-activated device, a patient-activated device, a display device or any other type of device capable of sending and receiving signals to and from IMD 10. Telemetry module 20 and remote device 28 are respectively coupled to antennas 26 and 30 for facilitating the wireless data transfer. Telemetry module 20 may be configured to perform any type of wireless communication. For example, telemetry module 20 may send and receive radio frequency (RF) signals, infrared (IR) frequency signals, or other electromagnetic signals. Any of a variety of modulation techniques may be used to modulate data on a respective electromagnetic carrier wave. Alternatively, telemetry module 20 may use sound waves for communicating data, or may use the patient's tissue as the transmission medium for communicating with a programmer positioned on the patients skin. In any event, telemetry module 20 facilitates wireless data transfer between IMD 10 and remote device 28. Telemetry module 20 includes wake-up receiver 32 for monitoring received communication signals and detecting whether incoming wake-up communication signals are being received from remote device 28. Wake-up receiver 32 may include one or more signal detectors 33 for detecting various signal quantity characteristics in the incoming communication signals.

Controller 24 may comprise any of a wide variety of hardware or software configurations capable of executing algorithms to control telemetry module 20, wake-up receiver 32, and other components. Example hardware implementations of controller 24 include implementations within an application specific integrated circuit (ASIC), a field programmable gate array (FPGA), a programmable logic device, specifically designed hardware components, one or more processors, or any combination thereof. If implemented in software, a computer readable medium, such as a memory in the IMD 10, may store computer readable instructions, e.g., program code, that can be executed by controller 24 to carry out one or more of the techniques described herein. For example, the memory may comprise random access memory (RAM), read-only memory (ROM), non-volatile random access memory (NVRAM), electrically erasable programmable read-only memory (EEPROM), flash memory, or the like. Telemetry module 20 may likewise comprise any of a wide variety of the above-listed hardware or software configurations capable of executing algorithms for facilitating wireless telemetry.

IMDs typically must rely entirely on an implanted power source, e.g., battery 22. It is desirous to keep the physical size of IMD 10 to a minimum, which further places limitations on the size of the implanted battery 22. The various components of IMD 10 (i.e., telemetry module 20, controller 24, wake-up receiver 32) rely on battery 22 for power. For embodiments of IMD 10 that have nonrechargeable batteries 22, IMD 10 must be surgically replaced when battery 22 is fully depleted. For embodiments of IMD 10 having rechargeable batteries 22, a surgical procedure is not required when battery 22 is depleted, however, battery 22 must be recharged more frequently since it cannot store as much energy. Thus, power conservation is particularly important in IMD 10. Further, consistently powering up wake-up receiver 32 of telemetry module 20 to perform sniff operations requires electrical power which can drain battery 22 of IMD 10 at an unacceptable rate.

In one or more embodiments, IMD 10 and a method for operating the same is provided in which telemetry module 20 is normally maintained in a power off or low power inactive "sleep" state in order to conserve power. Wake-up receiver 32 is then periodically powered up to perform sniff operations in which wake-up receiver 32 monitors communication channels in the desired communication frequencies (e.g., MICS band, MEDS band or any other frequency bands) to detect wake-up communication signals or other types of communication signals being received from remote device 28. If a communication signal from remote device 28 is detected during these sniff operations, it is determined that remote device 28 is either attempting to communicate with IMD 10 or remote device 28 is within telemetry range capable of communicating with IMD 10 (e.g., remote device 28 is transmitting beacon signals that are being received by IMD 10). IMD 10 can then power up ("wake-up") the necessary components required to transmit or receive data from remote device 28.

For typical RF communications, given the plethora of noise, interference sources, and other extraneous signals that exist (collectively referred to hereafter as "unwanted signals"), wake-up receiver 32 could unnecessarily consume current and thus waste the limited power resources of battery 22 if it were to implement detection procedures to discover whether these unwanted signals are actually wake-up signals. Thus, in accordance with one or more embodiments, a staged detection process is employed by the components of wake-up receiver 32, such as an RF detector, that reduces power consumption in IMD 10 during sniff operations by immediately aborting sniff operations as early in the sniff process as it is determined that the received communication signal is an unwanted signal.

In one or more embodiments, a sniff is processed in a plurality of detection stages in which each detection stage incrementally increases the accuracy of detecting whether the received communication signal is a wake-up communication signal. When measuring a quantity of a signal, such as its RF power or the frequency deviation of the signal, the standard deviation of the measurement is reduced as the measuring time or number of measurements is increased. However, measuring signal quantities for longer periods of time or to obtain a greater number of measurements also requires greater current consumption by the signal detector 33. Thus, in one or more embodiments, an RF signal detector in the wake-up receiver 32 employs a staged detection process in which the uncertainty in the signal quantity measurements of the received communication signal is incrementally reduced with each detection stage, while sniff processing is aborted during any of the detection stages as soon as it is determined that the received communication signal is likely to be an unwanted signal. When a measured signal quantity is far below a certain threshold after only a short measurement, then sniff processing can be aborted at an early stage of the staged detection process despite any uncertainty in the measurement because it can be assumed that the received communication signal is an unwanted signal. In this manner, the average current consumption of the RF signal detector 33 can be reduced by not wasting energy on received communication signals that are likely to be unwanted signals.

Figure 3:
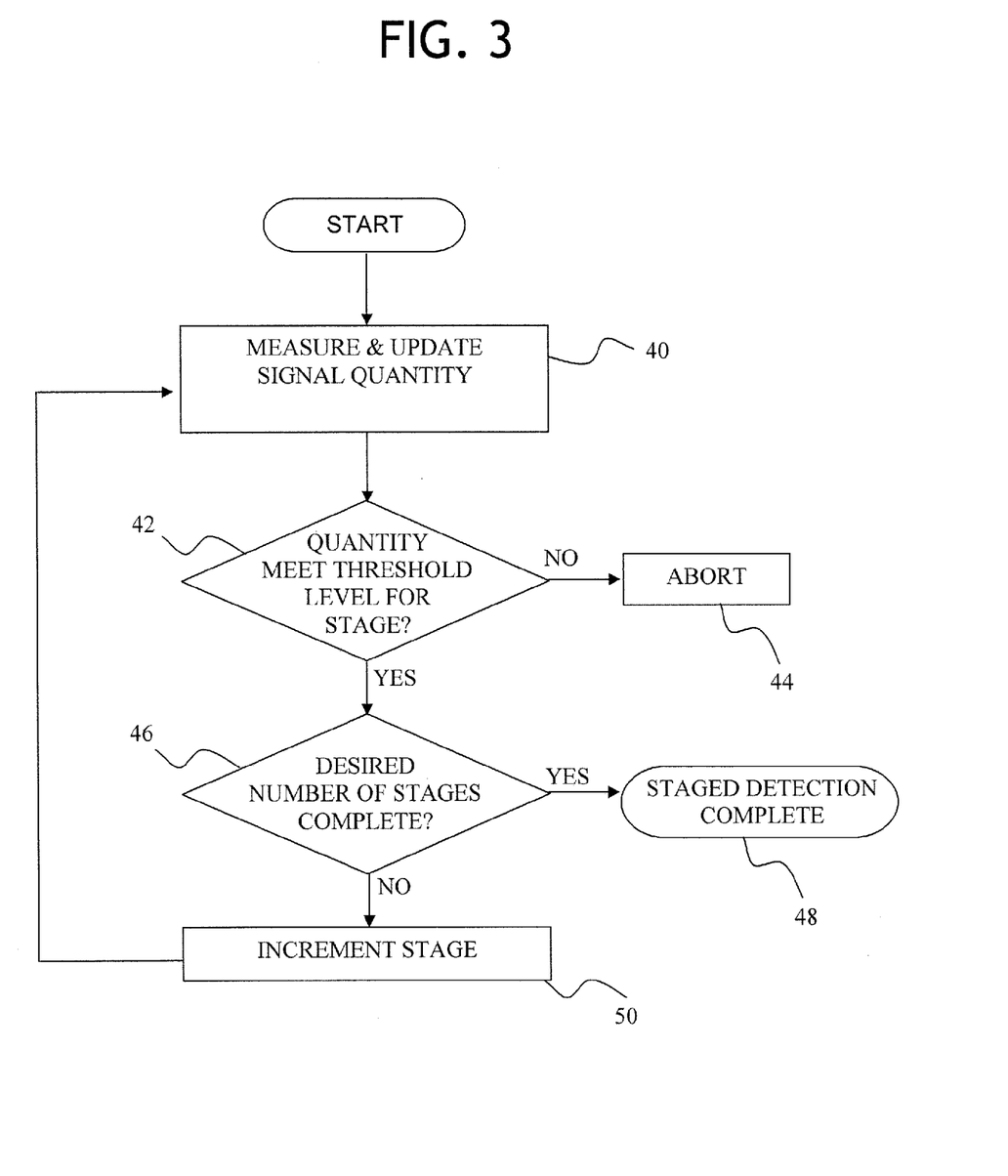
FIG. 3 is an operational flow diagram illustrating a process for implementing the staged detection process in accordance with one embodiment of the present disclosure.

An operational flow diagram is illustrated in FIG. 3 in accordance with one or more embodiments of the staged detection process employed in the wake-up receiver 32. Wake-up receiver 32 of telemetry module 20 is configured to operate in a low power or power off inactive mode until wake-up receiver 32 is activated to start sniff procedures for detecting the presence of wake-up signals or other communication signals. Once activated, a signal quantity of a received communication signal is measured (40). For example, the measured signal quantity may include the RF power or frequency deviation of the received communication signal or may comprise other measurable quantities. The measured signal quantity is compared against a corresponding threshold value for that stage (42). If it is determined that the measured signal quantity fails to meet a corresponding threshold level (e.g., the measured signal quantity is less than a certain threshold value or less than the certain threshold value by a certain degree), the staged detection process is aborted (44) and sniff operations are ceased on the received communication signal.

If the measured signal quantity meets the corresponding threshold value for that stage, a determination is made whether a desired number of detection stages have been completed (46). If so, then the staged detection process is complete (48). In one or more embodiments, once the staged detection process is complete, further signal processing operations can performed on the received communication signal. For example, other processes for authenticating its status as a wake-up signal can be performed (e.g., additional staged detection processes or other detection processes that investigate other characteristics of the received communication signal). Alternatively, the completion of the staged detection process can simply be used to signify that the tests performed on the measured signal quantity have been satisfied.

If the desired number of detection stages have not been completed (46), then the detection stage is incremented (50) and control returns to (40) where the next stage of the staged detection process is performed. In one or more embodiments, a combined signal quantity of the received communication signal is calculated by updating (40) the signal quantity measurements performed in prior stages with the new signal quantity measurement performed in the next stage. The combined signal quantity of the received communication signal is then compared against a corresponding threshold value for that respective stage. This incremental staged detection process is repeated until either the desired number of stages have been completed (48) or the staged detection process is aborted (44) and sniff operations are ceased on the received communication signal.

Figure 4:
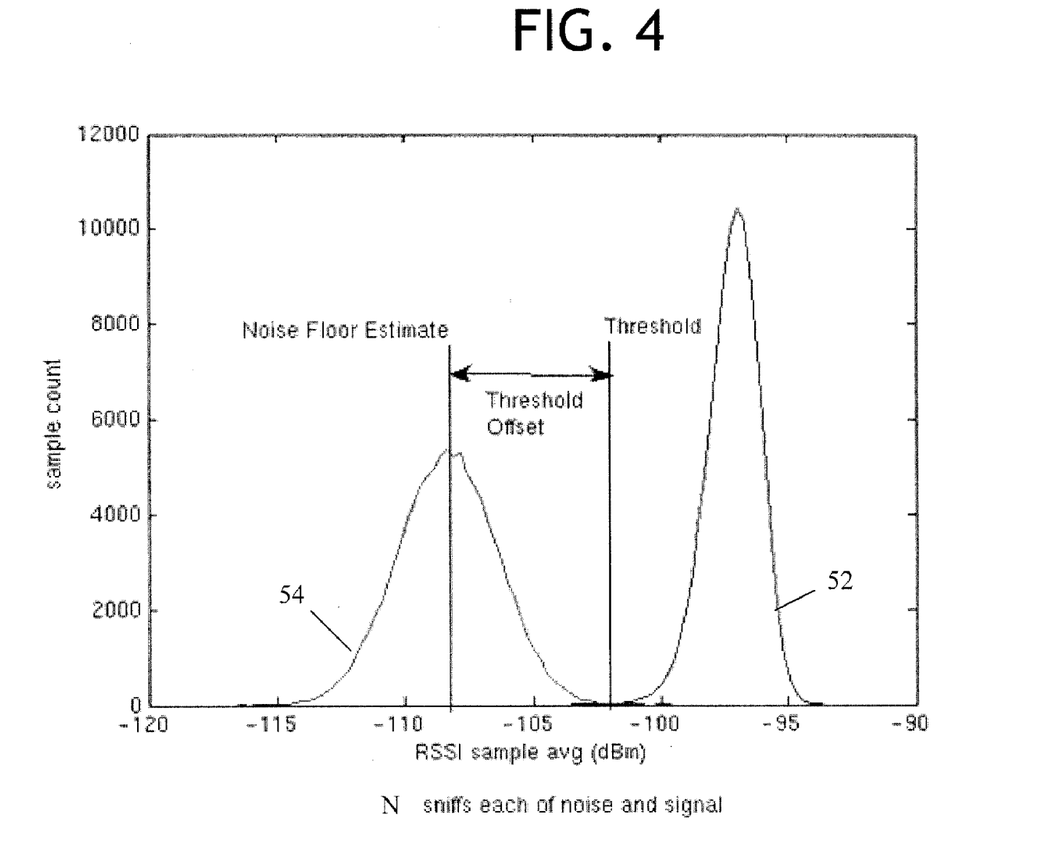
FIG. 4 is a graphical illustration of a representative RSSI sample average of noise and wake-up signals in accordance with one embodiment of the present disclosure.

In one or more embodiments, the signal quantity monitored during the staged detection process is the measured signal strength of the received communication signal, such that each signal strength measurement can be assigned a Received Signal Strength Indicator (RSSI) value. The RSSI value of the incoming signal is compared (42) to a threshold level for the particular stage at which the RSSI value is measured. In one or more embodiments, the threshold level is based on the estimated noise floor for the unwanted signals. For example, as illustrated in the sample representative graphical illustration of FIG. 4 depicting an RSSI sample average distribution of noise and valid wake-up signals for a large number of sniffs, a valid wake-up signal RSSI average would appear indicated by plot 52 above the threshold level while noise and other unwanted signals would have an RSSI average indicated by plot 52 below the selected threshold. The particular threshold and threshold offset may differ based on the particular band being sniffed (e.g., MICS and MEDS band may have different thresholds and threshold offsets) and the particular stage of the staged detection process.

Figure 5:
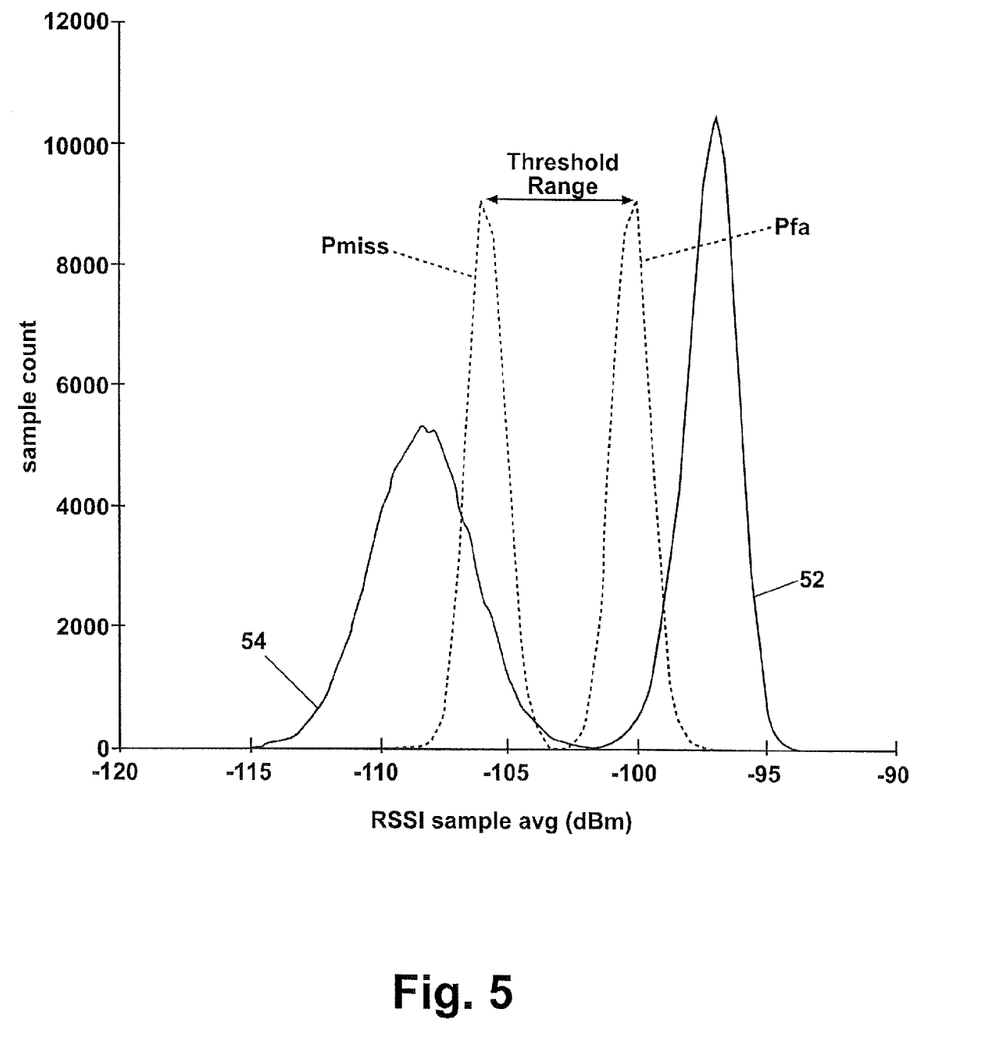
FIG. 5 is a graphical illustration of a representative RSSI sample average of noise and wake-up signals and the threshold range in accordance with one embodiment of the present disclosure.

If the threshold is selected to be too high, then certain valid wake-up communication signals that are received would be missed operations if their RSSI value were less than the selected threshold, resulting in the staged detection process aborting the sniff. The RSSI threshold value below which valid wake-up signals would be missed, with a specified probability (Pmiss), is referred to as the Pmiss threshold. If the threshold for the staged detection process is selected to be too low, then noise and other unwanted signals could present a 'false alarm' as valid wake-up signals if their RSSI value was greater than the selected threshold, thereby wasting valuable current consumption in having the RF signal detector perform processing on such 'false alarm' unwanted signals. The RSSI threshold value above which unwanted signals would generate 'false alarms' as wake-up signals, with a specified probability (Pfa), is referred to as the Pfa threshold. There exists a range of threshold values that will allow the staged detection process to meet both the Pmiss and Pfa requirements, where the difference between where Pmiss and Pfa thresholds is referred to as the threshold range or threshold offset, as illustrated in FIG. 5.

The staged detection process exploits the fact that the standard deviation of a signal quantity measurement is reduced as more time is spent measuring the signal quantity or more measurements of the signal quantity are obtained. Thus, the first RSSI measurement that is measured during a sniff will have a large standard deviation, while each successive RSSI measurement will produce a resulting average having a standard deviation that gets smaller as each additional sample is averaged in. Thus, accuracy of the comparison between RSSI measurements and the threshold is improved with each additional RSSI measurement.

Figure 6:
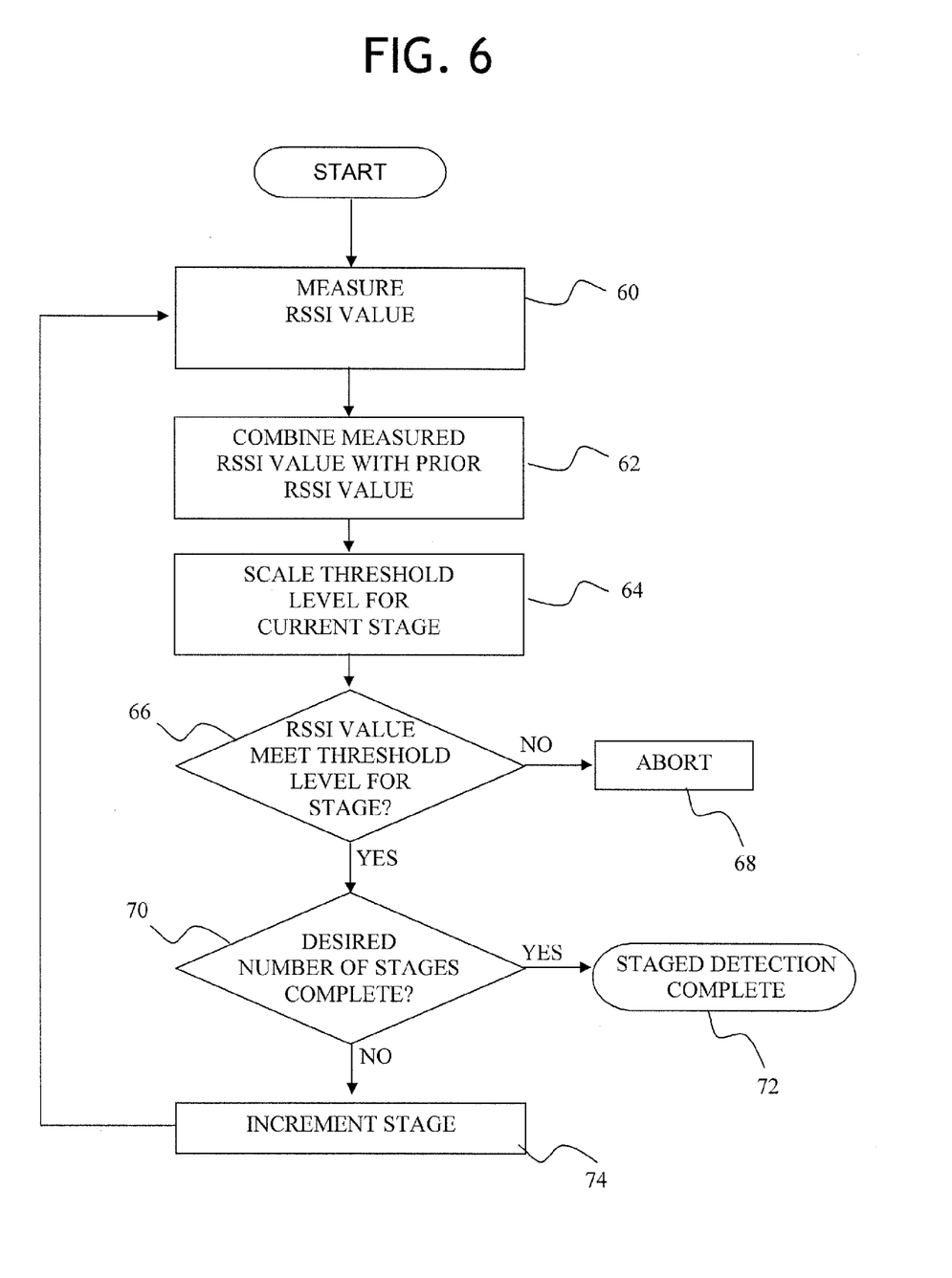
FIG. 6 is an operational flow diagram illustrating a process for implementing the staged detection process in accordance with one embodiment of the present disclosure.

Referring now to FIG. 6, an operational flow diagram is provided in accordance with one or more embodiments in which RSSI values are monitored in the staged detection process employed in the wake-up receiver 32. A RSSI value of a received communication signal is initially measured (60). A combined signal quantity of the received communication signal is calculated (62) by adding the RSSI value from the current stage of the staged detection process to the RSSI values obtained in signal quantity measurements performed in prior stages. Further, the threshold is scaled (64) to match the current stage of the staged detection process. In one embodiment, rather than measure a number of RSSI measurements and then compute an average of the RSSI measurements to compare against the threshold, a simplified implementation is provided in which an RSSI value from a current stage is simply added together with RSSI values measured from prior stages of the staged detection process and the total combined RSSI value is compared against a scaled threshold. For example, if the staged detection process is measuring the first RSSI value in the first stage, then the threshold is scaled by a factor of one. If the staged detection process is measuring the third RSSI value in the third stage, then the threshold is scaled by a factor of three (i.e., threshold value×3) and so on.

The combined signal quantity is compared against the corresponding scaled threshold value for that stage (66). If it is determined that the combined signal quantity fails to meet the corresponding scaled threshold level (e.g., the measured signal quantity is less than the scaled threshold value), the staged detection process is aborted (68) and sniff operations are ceased on the received communication signal. If the combined signal quantity meets the corresponding threshold value for that stage, a determination is made whether a desired number of detection stages have been completed (70). If so, then the staged detection process is complete (72). If the desired number of detection stages have not been completed, then the detection stage is incremented (74) and control returns to (60) where the next stage of the staged detection process is performed. By using multiple stages of detection in the staged detection process, the threshold range between wake-up signal misses (Pmiss) and 'false alarm' signals (Pfa) is increased with only a minimal increase in the average time to abort. Without multiple detection stages, the only other way to increase the threshold range would be to average a larger number of RSSI measurements before comparing their average against the threshold, which would linearly increase the average time to abort with the number of RSSI measurements that are averaged. Thus, the staged detection process reduces the average measurement time for an RF signal detector to reach a decision to abort sniff processing, thereby lowering the average current consumption of the RF detection, which is critical for ultra-low power applications.

In one or more embodiments, the signal quantity monitored during the staged detection process is a frequency deviation or another signal quantity.

The staged detection process may be implemented using a wide variety of possible hardware or software configurations. Example hardware implementations include controller 24 or other hardware implementations located in telemetry module 20, wake-up receiver 32 or one of its components that include implementations within an application specific integrated circuit (ASIC), a field programmable gate array (FPGA), a programmable logic device, specifically designed hardware components, one or more processors, or any combination thereof. If implemented in software, a computer readable medium, such as a memory in the IMD 10, may store computer readable instructions, e.g., program code, that can be executed by controller 24 or another hardware implementation to carry out the falsing protection algorithm described herein. For example, the memory may comprise random access memory (RAM), read-only memory (ROM), non-volatile random access memory (NVRAM), electrically erasable programmable read-only memory (EEPROM), flash memory, or the like. Further, wake-up receiver 32 may include signal detectors 33, such as RF detectors and the like, for monitoring the communication signals received by IMD 10.

In the methods and devices described herein, significant current consumption savings can be achieved alleviating wake-up receiver 32 from performing all phases of sniff processing when it becomes evident early that sniff processing should be aborted when it is determined that the received communication signal is an unwanted signal. Power consumption of wake-up receiver 32 is further reduced by avoiding sniff processing of signals that are likely to cause false alarms or false indications of wake-up signals.

While the staged detection process is described in various embodiments in connection with detecting whether valid wake-up signals are being received in IMD 10, it is understood that the staged detection process could likewise be utilized in other signal receiving devices requiring the detection of certain signal quantity characteristics in a low power manner.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A method comprising:
   operating an implanted medical device capable of receiving wireless communication signals; and
   monitoring a communication signal received in a receiver in the implanted medical device using a staged detection process to detect characteristics of the received communication signal, the staged detection process further comprising:

performing a desired number of stages of measurements of a signal quantity of the received communication signal, wherein a combined signal quantity of the received communication signal is calculated by updating the signal quantity measurements performed in prior stages with signal quantity measurements performed at each stage, comparing the combined signal quantity of the received communication signal at each measurement stage against a corresponding threshold value for that stage, and aborting the staged detection process if the combined signal quantity fails to meet the corresponding threshold value for that stage.

2. The method of claim 1, further comprising selecting the desired number of stages of measurements to achieve a desired standard deviation of the signal quantity measurements.

3. The method of claim 1, further comprising selecting the desired number of stages of measurements to achieve a desired level of certainty in the comparison between the combined signal quantity of the received communication signal and its corresponding threshold value.

4. The method of claim 1, wherein the measured signal quantity is a frequency deviation.

5. The method of claim 1, wherein the measured signal quantity is a strength of the received communication signal.

6. The method of claim 5, further comprising:
calculating the combined signal quantity by adding the signal quantity measurement for a current stage of the staged detection process to the signal quantity measurements from prior stages;

scaling the corresponding threshold value for the current stage of the staged detection process;

comparing the combined signal quantity of the received communication signal at the current stage of the staged detection process against the scaled threshold value for that stage; and aborting the staged detection process if the combined signal quantity fails to meeting the scaled threshold value for that stage.

7. The method of claim 1, further comprising indicating a passing state of the staged detection process of the received communication signal if the staged detection process is not aborted.

8. A low power, wake-up communication signal detector in an implantable medical device comprising:
a receiver configured to detect a communication signal being received from a remote device; and
a signal detector configured to monitor the communication signal received using a staged detection process to detect whether the received communication signal is a wake-up communication signal intended for the implanted medical device, wherein the signal detector is further configured perform the staged detection process by:
performing a desired number of stages of measurements of a signal quantity of the received communication signal, wherein a combined signal quantity of the received communication signal is calculated by updating the signal quantity measurements performed in prior stages with signal quantity measurements performed at each stage, comparing the combined signal quantity of the received communication signal at each measurement stage against a corresponding threshold value for that stage, and aborting the staged detection process if the combined signal quantity fails to meeting the corresponding threshold value for that stage.

9. The wake-up communication signal detector of claim 8, wherein the desired number of stages of measurements are selected to achieve a desired standard deviation of the signal quantity measurements.

10. The wake-up communication signal detector of claim 8, wherein the desired number of stages of measurements are selected to achieve a desired level of certainty in the comparison between the combined signal quantity of the received communication signal and its corresponding threshold value.

11. The wake-up communication signal detector of claim 8, wherein the measured signal quantity is a frequency deviation.

12. The wake-up communication signal detector of claim 8, wherein the measured signal quantity is a strength of the received communication signal.

13. The wake-up communication signal detector of claim 12, wherein the signal detector is further configured perform the staged detection process by:
calculating the combined signal quantity by adding the signal quantity measurement for a current stage of the staged detection process to the signal quantity measurements from prior stages;

scaling the corresponding threshold value for the current stage of the staged detection process;

comparing the combined signal quantity of the received communication signal at the current stage of the staged detection process against the scaled threshold value for that stage; and aborting the staged detection process if the combined signal quantity fails to meeting the scaled threshold value for that stage.

14. A telemetry module in an implantable medical device comprising:
wake-up receiver means configured to perform sniff operations for detecting whether a wake-up communication signal is being received by the implantable medical device; and
signal detector means for monitoring a communication signal received in a receiver in the implanted medical device using a staged detection process to detect characteristics of the received communication signal, the staged detection process further comprising:
performing a desired number of stages of measurements of a signal quantity of the received communication signal, wherein a combined signal quantity of the received communication signal is calculated by updating the signal quantity measurements performed in prior stages with signal quantity measurements performed at each stage, comparing the combined signal quantity of the received communication signal at each measurement stage against a corresponding threshold value for that stage, and aborting the staged detection process if the combined signal quantity fails to meet the corresponding threshold value for that stage.

15. The telemetry module of claim 14, wherein the desired number of stages of measurements is selected to achieve a desired standard deviation of the signal quantity measurements.

16. The telemetry module of claim 14, wherein the desired number of stages of measurements is selected to achieve a desired level of certainty in the comparison between the combined signal quantity of the received communication signal and its corresponding threshold value.

17. The telemetry module of claim 14, wherein the measured signal quantity is a frequency deviation.

18. The telemetry module of claim 14, wherein the measured signal quantity is a strength of the received communication signal.

19. The telemetry module of claim 14, wherein the staged detection process performed by the signal detector means further comprises:

calculating the combined signal quantity by adding the signal quantity measurement for a current stage of the staged detection process to the signal quantity measurements from prior stages;

scaling the corresponding threshold value for the current stage of the staged detection process;

comparing the combined signal quantity of the received communication signal at the current stage of the staged detection process against the scaled threshold value for that stage; and aborting the staged detection process if the combined signal quantity fails to meet the scaled threshold value for that stage.

* * * * *